United States Patent [19]

Wool

[11] Patent Number: 4,585,413
[45] Date of Patent: Apr. 29, 1986

[54] ORTHODONTIC DEVICE

[76] Inventor: Arthur L. Wool, 1402 Penn Ave., Wyomissing, Pa. 19610

[21] Appl. No.: 687,727

[22] Filed: Dec. 31, 1984

[51] Int. Cl.⁴ ............................................. A61C 3/00
[52] U.S. Cl. .......................................... 433/8; 433/14; 433/15
[58] Field of Search ................... 433/8, 9, 10, 11, 13, 433/14, 15, 16

[56] References Cited

U.S. PATENT DOCUMENTS

| 2,705,367 | 4/1955 | Berke | 433/8 |
| 2,759,265 | 8/1956 | Johnson | 433/13 |
| 2,908,974 | 10/1959 | Stifter | 433/16 |
| 3,128,552 | 4/1964 | Broussard | 433/13 |
| 3,238,619 | 3/1966 | Brunson et al. | 433/13 |
| 4,107,844 | 8/1978 | Kurz | 433/11 |
| 4,180,912 | 1/1980 | Kesling | 433/8 |
| 4,242,085 | 12/1980 | Wallshein | 433/16 |
| 4,355,975 | 10/1982 | Fujita | 433/11 |
| 4,416,627 | 11/1983 | Beazley | 433/8 |

FOREIGN PATENT DOCUMENTS

| 1184451 | 12/1964 | Fed. Rep. of Germany | 433/8 |
| 2903768 | 8/1980 | Fed. Rep. of Germany | 433/8 |

Primary Examiner—John J. Wilson
Attorney, Agent, or Firm—Antonelli, Terry & Wands

[57] ABSTRACT

An orthodontic device adapted for lightwire or rectangular or square arch wire treatment having a bracket which is bonded to a patient's tooth, a face for hiding the bracket, and a slot defined by the bracket and face for receiving lightwire or rectangular or square arch wire.

23 Claims, 9 Drawing Figures

ORTHODONTIC DEVICE

BACKGROUND OF MY INVENTION

The present invention relates to an improved orthodontic device and, more particularly, to an orthodontic bracket which is more cosmetically aesthetic, is adaptable for lightwire or rectangular or square arch wire treatment, and which can utilize arch wire fixation devices in the form of steel ligature wire, elastomeric ring, and single lock pin and the like.

Devices for the treatment of malocclusion or, in layman's terms, an abnormality in the coming together of teeth have been known and used for a long time. However, it has also been generally recognized that such devices are often unsightly or extremely limited in versatility, thus requiring various types of devices to accomplish different orthodontic goals in treating persons with diverse malocclusion problems.

One conventional technique is to treat the malocclusion from the lingual or palatal side. However, as discussed in U.S. Pat. No. 4,209,906, new orthodontic methods for treating this condition use the firm affixation of a bracket to the labial or buccal surfaces of the patient's teeth and the insertion and fixation of a wire into these brackets to correct misalignment of the teeth through the elastic force of the wire. A lightwire technique can be used whereby the wire is inserted from the top or bottom of the bracket. Alternatively, edgewise rectangular wire has been used by sliding the arch wire through a slot longitudinally. Fixation of the arch wire in the brackets is made by means of lock pins. This technique provides somewhat more versatility than treating malocclusion from the lingual or palatal side. However, the brackets, particularly buccal tubes, are completely visible in the patient's mouth. Furthermore, many prior designs have been found in practice to be impractical in light of real-life conditions, namely substantial misalignment of the patient's teeth which make it impossible to engage various types of locking devices.

The aforementioned U.S. Pat. No. 4,209,906 shows several variations of two bracket types. Bracket-and-wire arrangements take many other forms as well. Indeed, that is one of the problems to which my invention is addressed. As will be readily apparent, the prior art arrangements are not particularly aesthetic, dictated as they are by functional requirements. However, recent proposals have recognized that cosmetic values in the design of the brackets are very much a part of the treatment and thus are functional aspects which must be taken into account, particularly since the brackets are visible to others due to their bonding to the labial or buccal surfaces. Almost all patients, young or old, are self-conscious about wearing an orthodontic brace which detracts from facial appearance. For this reason, many persons forego needed treatment, while those who do undergo treatment suffer psychologically.

To overcome this problem, one proposal has been to use separate tooth colored or gray looking caps which serves in place of a lock pin to retain arch wires while, at the same time, serving to provide maximum aesthetics and comfort from stainless steel brackets. These caps can be molded from LEXAN and provided with locking tabs to secure themselves to the brackets. Usually, however, they require placement by use of a special instrument, although it is possible to place them by hand.

SUMMARY OF MY INVENTION

It is a main object of my invention to overcome the problems and disadvantages encountered in using conventional orthodontic brackets for the treatment of malocclusion from the buccal or labial surfaces.

It is a further object of my invention to provide a simple orthodontic bracket which is versatile while, at the same time, more comfortable and far less unsightly than previous orthodontic bracket arrangements.

It is still a further object of my invention to provide an orthodontic bracket which is adaptable for lightwire and for rectangular or square arch wire treatment and which can incorporate three wire fixation devices so as to provide rotation control.

The foregoing objects and advantages have been obtained by the invention of a labial/buccal bonded bracket usable for lightwire treatment or for edgewise rectangular arch wire and having a cosmetic facade behind which a wire, elastomeric ring and lockpin can be inserted with a minimum amount of cosmetic disruption to the patient's mouth caused by wearing the brackets.

BRIEF DESCRIPTION OF THE DRAWING

These and further features, objects and advantages of my invention will become readily apparent from the following detailed description when taken in conjunction with the accompanying drawing which shows, for purposes of illustration of the principles of my invention only, several embodiments of the present invention and wherein.

DETAILED DESCRIPTION OF PREFERRED EMBODIMENTS

Figure 1:
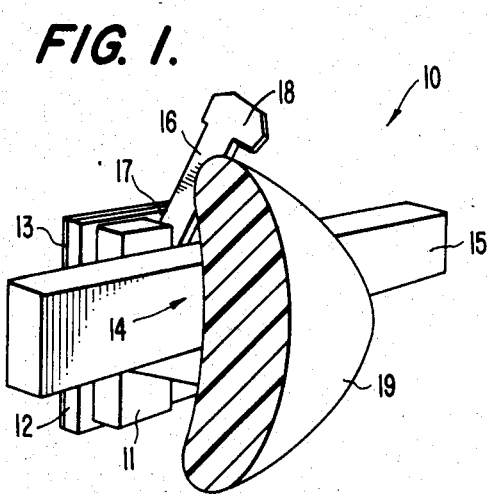
FIG. 1 is a perspective view of one embodiment of my invention showing a bracket with flat base, in which a portion of the facade of the bracket is shown (i.e. the face is shown in cross-section) and the lock pin is partially inserted in the slot after a rectangular arch wire has been inserted.
Figure 2:
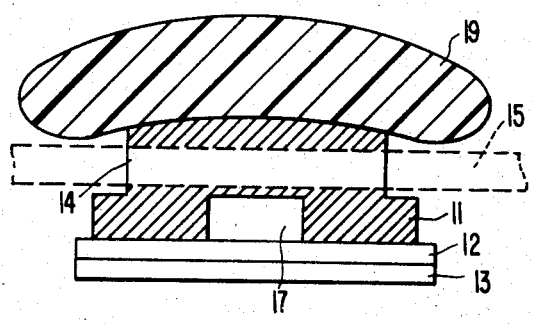
FIGS. 2 through 4 are top partial-sectional views of a bracket of the type shown in FIG. 1 with the facade and bracket shown in sectional view and also showing various lock pin slot configurations and, in the case of FIG. 3, a curved base and pad with the lock pin is shown in dotted lines.
Figure 3:
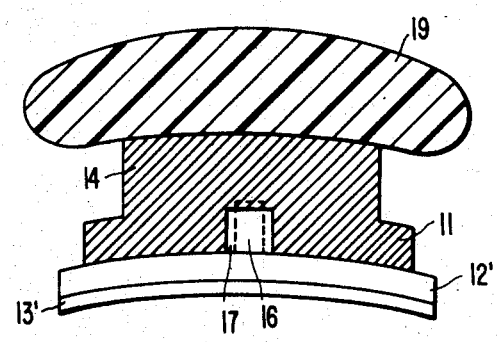
Figure 4:
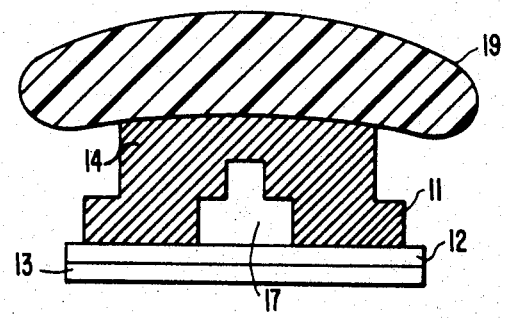

Referring now to the drawing and, in particular to FIG. 1, there is shown in perspective view one presently preferred embodiment of my improved orthodontic device designated generally by the numeral 10. The device 10 consists of a bracket 11 made from standard orthodontic materials, such as stainless steel or polycarbonate, used for similar purposes. The bracket 11 is designated to be attached to the labial or buccal surfaces of the teeth and for this reason can be provided with a flat base 12 for maximum rotational control, or a curved base 12', as shown in FIG. 3, at the tooth attaching surface. For example, the curved base 12' can take the shape of cuspid/bicuspid curvature, a lower anterior curvature, or to individual tooth shapes in a conventional manner. The base 12, 12' can be provided with bonding pads 13, 13' respectively which are also well known. For example, the bonding pads 13 or 13' which provide both shear and tensile strength, can be made from foil mesh. Of course, it should be clearly understood that the bracket according to my invention can be provided without pads.

The bracket 11 has a square or rectangular notched or slotted portion 14 defined by the bracket 11 and the back face of the facade for receiving a rectangular arch wire 15 of substantially the same width as the width of the notch or slot. Although a rectangular wire has been shown, square arch wire could be used, if desired. Alternatively, round lightwire can be used where such treatment is desired. Although the invention is not particularly limited thereto, it has been found that forming the slotted portion with a width of between 0.018 to 0.022 inch. In particular, a width of 0.022 inch is highly advantageous because it allows the use of 0.022×0.022 square wire, 0.022×0.016 rectangular wire, 0.022×0.028 rectangular wire or 0.022 round lightwire, which are all generally quite useful sizes for many orthodontic applications.

To prevent the arch wire or lightwire from escaping from the bracket, standard lock pins 16 can be utilized. These lock pins, which are usually made of brass or stainless steel, have tapered shafts for easy introduction into a slot 17, after which the tail of the pin 16 is bent around the bracket 11. They are also conventionally designed in such a way that the head 18 of the pin 16 assures tipping freedom of arch wire 15 and unimpaired distal sliding. Moreover, the pin 16 can be provided with a rounded head for further patient comfort. However, it is to be clearly understood that my invention is not limited to a particular design of lock pin. For instance, the lock pin can be provided with a wedge head design (not shown) without departing from the scope of my invention.

Figure 5:
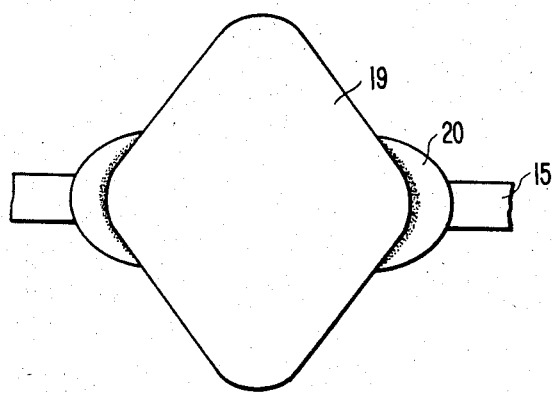
FIGS. 5 and 6 are front elevational views of two different embodiments of the bracket according to my invention wherein the former uses an elastomeric ring around the back side of the facade to secure the arch wire and the latter uses a separate ligature wire around the back side of the facade.
Figure 6:
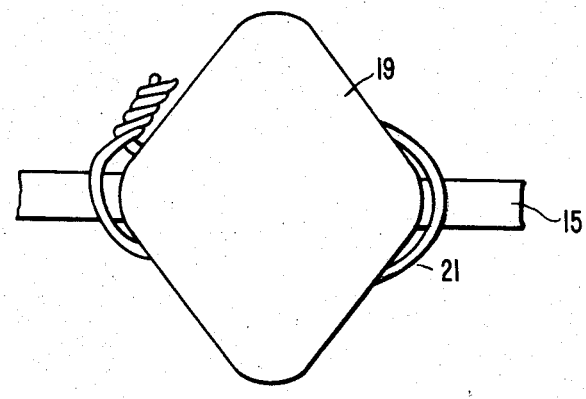

The bracket 11 extends between the base 12 outwardly to connect with a front piece or face 19 which covers or hides the entire structure, including the pad. Although the bracket face has no groove, nevertheless the bracket can be used to accept rectangular or square arch wire edgewise in the slot or round lightwire from the top with either a lock pin 16 and/or with elastomeric rings 20 as shown in FIG. 5 and/or with ligature steel wire 21 as shown in FIG. 6 to secure the wire in place. The slot 14 for the arch wire 15 is arranged so that it is not necessary to feed the end of the arch wire through and behind the slot to effect ligation. After the wire 15 is in its desired position, ligature can be accomplished with steel ligature wire 21, elastomeric ring 20 or the conventional single lock pins 16 in a conventional manner.

Figure 7:
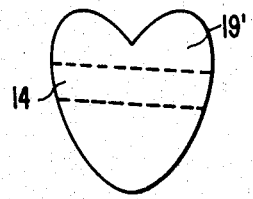
FIG. 7 is a front view of another embodiment of my invention in which the face has a different configuration.
Figure 8:
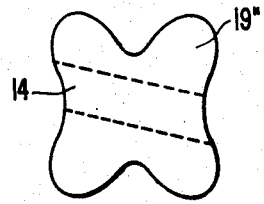
FIGS. 8 and 9 are front views of yet other embodiments with other face configurations.
Figure 9:
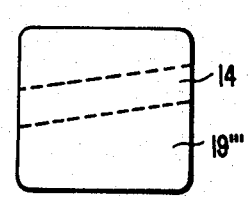

The face 19 can be configured in the shape shown in FIGS. 1, 5 and 6 and made from a synthetic material such as LEXAN which can be colored to match the patient's teeth. Alternatively, it can be made from the same material as the bracket itself. Generally speaking, the face 19 has rounded or streamlined contours to provide for greater patient comfort when the bracket comes in contact with the labia or with the cheeks. The shape of the face can be different for different tooth types, e.g. molars, canines, bicuspids, and also can be more individually matched to the particular patient's teeth if desired, both in color or shape. Different shapes are shown for illustrative purposes only in FIGS. 7 to 9. In particular, it should be noted that using a square arrangement such as shown in FIG. 9 (or a rectangular one) has an advantage of giving a large tie wing area. Also, square and rectangular shapes are more conventional in the sense of being closer in appearance to existing brackets in overall shape.

Finally, my invention as shown in FIGS. 1 through 7 shows a slot 14 which is neither torqued nor angulated. However, my invention contemplates that the slots for receiving the wire can be torqued and/or angulated in a known manner depending upon the tasks which have to be accomplished and the direction in which more force is necessary. Angulation of the slot 14 is shown in FIGS. 8 and 9. Nevertheless, all brackets will look essentially the same due to the facade 19 which hides the brackets. Furthermore, the brackets can be inverted so that the lightwire or rectangular or square arch wire is inserted from the bottom rather than from the top of the bracket.

While these and other features, objects and advantages of my invention will become readily apparent to those skilled in the art from the foregoing description, it should be understood that the same is susceptible of changes and modifications without departing from the scope of my invention. Therefore, I do not intend to be limited to the details shown and described in this application but intend to cover all such changes and modifications as are encompassed with the scope of the appended claims.

I claim:

1. An orthodontic bracket for use with lightwire or rectangular or square arch wire, comprising a mounting means adapted to be securely fastened to a patient's tooth, slot means provided on the bracket for receiving said lightwire or arch wire in an occlusal or gingival direction and a facade means fixedly associated with the mounting means for covering the mounting means as well as lightwire or arch wire in the bracket used in treatment of a patient's teeth so that only said facade means of said device is visible from the front, wherein said facade means is formed to be an integral, non-removable part of said bracket.

2. An orthodontic bracket in accordance with claim 1, wherein additional slot means is provided on the bracket, and a locking pin is adapted to be received in the additional slot means for securing the lightwire or the arch wire.

3. An orthodontic bracket in accordance with claim 2, wherein the slot means is angulated.

4. An orthodontic bracket according to claim 1, wherein an elastomeric ring is provided on the bracket between the facade means and the patient's tooth for securing the arch wire in the slot means.

5. An orthodontic bracket in accordance with claim 4, wherein the slot means is torqued.

6. An orthodontic bracket in accordance with claim 4, wherein additional slot means is provided on the bracket, and a locking pin is adapted to be received in the additional slot means for securing the lightwire or the arch wire.

7. An orthodontic bracket in accordance with claim 1, wherein a ligature wire is provided on the bracket between the facade means and the patient's tooth for securing the arch wire in the slot means.

8. An orthodontic bracket in accordance with claim 7, wherein additional slot means is provided on the bracket, and a locking pin is adapted to be received in the additional slot means for securing the lightwire or the arch wire.

9. An orthodontic bracket according to claim 7, wherein said ligature wire is formed of steel.

10. An orthodontic bracket according to claim 1 wherein said slot means has a width between 0.018 to 0.022 inch.

11. An orthodontic bracket according to claim 1 wherein said slot means has a width of substantially 0.022 inch.

12. An orthodontic bracket for use with lightwire or rectangular or square arch wire, comprising a mounting means adapted to be securely fastened to a patient's tooth, slot means provided on the bracket for receiving said lightwire or arch wire in an occlusal or gingival direction and a unitary facade means fixedly associated with the mounting means for covering the mounting means as well as lightwire or arch wire in the bracket used in treatment of a patient's teeth so that only said facade means of said device is visible when said device is viewed from the front, wherein said facade means is formed to be an integral, non-removable part of said bracket.

13. An orthodontic bracket in accordance with claim 12, wherein said device further includes additional slot means provided on the bracket adapted to receive a locking pin for securing the lightwire or the arch wire.

14. An orthodontic bracket acording to claim 13 further comprising means for joining said facade means to the mounting means and serving as the bottom surface of said slot means, wherein said joining means is adapted to receive an elastomeric ring or a ligature wire to secure the arch wire to the joining means behind the facade means so that the portion of said arch wire secured to the joining means is completely covered by said facade means.

15. An orthodontic bracket according to claim 14 wherein said ligature wire is formed of steel.

16. An orthodontic bracket according to claim 14 wherein said slot means has a width between 0.018 to 0.022 inch.

17. An orthodontic bracket according to claim 14 wherein said slot means has width of substantially 0.022 inch.

18. An orthodontic bracket according to claim 12 further comprising means for joining said facade means to the mounting means and serving as the bottom surface of said slot means, wherein said joining means is adapted to receive an elastomeric ring or a ligature wire to secure the arch wire to the joining means behind the facade means so that the portion of said arch wire secured to the joining means is completely covered by said facade means.

19. An orthodontic bracket according to claim 18 wherein said ligature wire is formed of steel.

20. An orthodontic bracket according to claim 18 wherein said slot means has a width between 0.018 to 0.022 inch.

21. An orthodontic bracket according to claim 18 wherein said slot means has a width of substantially 0.022 inch.

22. An orthodontic bracket according to claim 12 wherein said slot means has a width between 0.018 to 0.022 inch.

23. An orthodontic bracket according to claim 12 wherein said slot means has a width of substantially 0.022 inch.

* * * * *